United States Patent
Kozliak et al.

(10) Patent No.: US 7,781,638 B2
(45) Date of Patent: Aug. 24, 2010

(54) PHOTOCATALYST-INDUCED REDUCTION OF SEMIVOLATILE ORGANIC CHEMICALS ABSORBED IN SOLID MATERIALS

(75) Inventors: Evguenii I. Kozliak, Grand Forks, ND (US); Wayne Seames, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 383 days.

(21) Appl. No.: 11/209,144

(22) Filed: Aug. 22, 2005

(65) Prior Publication Data

US 2006/0207870 A1    Sep. 21, 2006

Related U.S. Application Data

(60) Provisional application No. 60/603,080, filed on Aug. 20, 2004.

(51) Int. Cl.
| | |
|---|---|
| A62D 3/30 | (2007.01) |
| A62D 3/34 | (2007.01) |
| A62D 101/20 | (2007.01) |
| A62D 101/22 | (2007.01) |
| A62D 101/26 | (2007.01) |
| A62D 101/28 | (2007.01) |

(52) U.S. Cl. .................. 588/313; 588/316; 588/405; 588/406; 588/408; 588/409

(58) Field of Classification Search ............... 588/405, 588/406, 400, 313, 316, 408, 409; 204/157.15
See application file for complete search history.

(56) References Cited

U.S. PATENT DOCUMENTS

| 5,604,339 | A | 2/1997 | Tabatabaie-Raissi et al. |
| 6,699,577 | B2 * | 3/2004 | Nonoyama et al. .......... 428/323 |
| 2004/0073078 | A1 * | 4/2004 | Osada et al. ................ 588/213 |

OTHER PUBLICATIONS

C. Antunes, et al., "Early stages in the $TiO_2$-photocatalyzed degradation of simple phenolic and non-phenolic lignin model compounds", from Journal of Photochemistry and Photobiology A: Chemistry 163, pp. 453-462 (2004).

S. I. Kuzina, et al., "Free Radicals in the Photolysis and Radiolysis of Polymers: IV. Radicals in γ- and UV-Irradiated Wood and Lignin", from High Energy Chemistry, vol. 38, No. 5, pp. 298-305 (2004).

L. R. C. Barclary, et al., "Peroxidations initiated by lignin model compounds: investigating the role of singlet oxygen in photo-yellowing", from Can. J. Chem. 76, pp. 1805-1816 (1998).

C. Steelink, et al., "On the Nature of Free-Radical Moiety in Lignin", from Journal of American Chemical Society, pp. 4048-4049 (Oct. 4, 1963).

* cited by examiner

*Primary Examiner*—Wayne Langel
*Assistant Examiner*—James Fiorito
(74) *Attorney, Agent, or Firm*—Kinney & Lange, P.A.

(57) ABSTRACT

A method, using a photocatalyst, to accelerate the reduction of semivolatile organic chemicals absorbed into porous, solid materials. The porous, solid material having absorbed one or more semivolatile organic contaminants. The photocatalytic material located on the surface of the porous, solid material is exposed to a light source, under aerobic conditions, which excites the photocatalyst and results in the reduction of the absorbed semivolatile organic chemical contaminants.

29 Claims, No Drawings

PHOTOCATALYST-INDUCED REDUCTION OF SEMIVOLATILE ORGANIC CHEMICALS ABSORBED IN SOLID MATERIALS

This application claims priority from U.S. Provisional Application No. 60/603,080 filed Aug. 20, 2004 for PHOTOCATALYST-INDUCED REDUCTION OF NONVOLATILE ORGANIC CHEMICALS ABSORBED IN SOLID MATERIALS.

BACKGROUND OF THE INVENTION

Porous, solid materials such as concrete, wood, gypsum, brick and like materials can become contaminated with semivolatile organic chemicals which pose a sizeable risk to human health. Semivolatile organic chemicals, such as fuel oil, diesel, and other transportation fuels, come in contact and can be absorbed into porous, solid materials, typically as a result of spills, leakage, and/or catastrophic floods. Other sources of contaminating semivolatile organic chemicals include household chemicals, solvents, pesticides, herbicides, insecticides, and other industrial chemicals that can be absorbed into porous materials due to commercial, industrial or home use. Semivolatile organic chemicals can also be absorbed into porous materials due to intentional acts of sabotage where these organic chemicals are used as chemical warfare agents or delivered in conjunction with other chemical warfare agents.

Past work has shown that non-aqueous phase liquids, both hydrophobic and hydrophilic, can get entrapped with water inside the pore spaces of materials and result in the formation of so-called "ganglia". The concrete, brick, tile, and wood used in buildings are all porous materials that can become contaminated by these non-aqueous or organic chemicals. The problem of non-aqueous phase liquid removal from ganglia in contaminated porous materials has been addressed in a number of publications known in the art. Both light and dense hydrocarbons, as well as chlorinated solvents, have been efficiently removed by heating, steam extraction, permanganate or Fenton reagent oxidation, surfactant flushing, and/or various pump-and-treat technologies. These publications, however, are limited to particular kinds of soil, mostly clay and sand.

These technologies are not suitable to clean bulky, contaminated building materials that are porous, solid materials with pore sizes less than 1 micrometer. Furthermore, heating and steam treatments, instead of removing contaminants, will only force the contaminants deeper into the material. Alternatively, other methods such as chemical treatment by bleach and other oxidizing agents will not remove the chemicals trapped in pores at all, they will only be able to remove minor contaminants located on the surface.

The inefficiency of pump-and-treat technologies became evident during the cleanup activities associated with the devastating 1997 flood of Grand Forks, North Dakota. The basements and first story walls of many buildings were contaminated with fuel oil. After numerous treating and washing cycles, there was minimal or no apparent reduction of fuel oil vapors within the air space of the basements of the flooded buildings. As a consequence, owners were forced to demolish structurally sound buildings due to the unhealthy air space within the buildings. Therefore, it is desirable to develop a method to efficiently and effectively reduce the concentration of semivolatile organic chemicals from porous, solid materials.

Photocatalyst-induced removal of hydrocarbons has been used in applications where the contaminated substance is either liquid or air. In addition, the use of photocatalysts to destroy formaldehyde leakage from a wood layer was previously described in U.S. Pat. No. 5,604,339. The 5,604,339 patent was aimed at destroying formaldehyde, a harmful toxic high volatile organic compound. The high volatility of formaldehyde facilitated its relatively easy breakdown from surfaces of the wood.

The present invention, however, demonstrates how photocatalysts can be used to reduce the amount of semivolatile organic chemicals absorbed into porous, solid materials upon application of the photocatalysts to the surface, followed by excitation with a light source under aerobic conditions for a period of one day or longer.

BRIEF SUMMARY OF THE INVENTION

The present invention is a method of accelerating the reduction in the concentration of one or more semivolatile organic chemicals from porous, solid materials using a photocatalyst and a light source. A photocatalyst on the surface of the contaminated solid material is exposed to a light source under aerobic conditions. The present invention is further directed to the application of photocatalysts to the surface of the contaminated solid material and subsequently exposing the photocatalyst to a light source under aerobic conditions to reduce the amount of semivolatile organic chemicals in the porous, solid material.

DETAILED DESCRIPTION OF INVENTION

In the present invention a method is described wherein a photocatalyst is applied to a porous, solid material to effectively reduce the level of semivolatile organic chemicals absorbed into that material. The present invention is designed to take advantage of this finding through the following aspects:

In the first aspect of the invention, a method of reducing the amount of semivolatile organic chemicals contained in porous, solid material by exposing a photocatalyst on the surface of a solid material to an appropriate light source under aerobic conditions.

In the second aspect of the invention, a method of reducing of the amount of semivolatile organic chemicals contained in porous, solid materials, wherein the semivolatile organic chemicals are broken down by a photocatalyst on the surface of the solid material upon exposure to an appropriate light source under aerobic condition.

In the third aspect of the invention, semivolatile organic chemicals are organic chemical compounds having a vapor pressure of less than 400 Pa at room temperature, and more preferably, vapor pressure of less than 200 Pa, 100 Pa, 50 Pa and 10 Pa. Chemical compounds include, but are not limited to, fuel oil/diesel/kerosene hydrocarbons (such as hexadecane), oxygenated compounds (such as diethyl phthalate), polychlorobiphenyls, halogenated compounds (such as DDT, chlordane, chlorinated dioxins and dibenzophanes), and nitrocompounds (such as nitroglycerin, nitrotoluene or trinitrotoluene).

In the fourth aspect of the invention, porous, solid materials include those materials used in building and construction. More preferably, porous solid materials include concrete, wood, lumber, gypsum, brick, masonry, asphalt, cement, cinder, tile, drywall and like materials.

In the fifth aspect of the invention, photocatalysts are biological, chemical or combinations thereof.

In the sixth aspect of the invention, photocatalysts are those chemical substances that include, but are not limited to, titanium dioxide, vanadium (V) oxide, $La_2Ti_2O_7$, Tinolux BBS, or combinations thereof, with and without additives.

In the seventh aspect of the invention, photocatalysts are those biological substances that include, but are not limited to, lignin.

In the eighth aspect of the invention, light sources include those producing visible and ultraviolet light. More preferably, the light source is a source of light that contains some form of ultraviolet light, for example natural light or fluorescent light.

In the ninth aspect of the invention, the photocatalyst is exposed to light for at least 1 day or longer. More preferably, the photocatalyst is exposed for at least 2 days, 3 days, 4 days, 5 days, 6, days or longer. Most preferably, the photocatalyst is exposed for at least 1 week, 2 weeks, 3 weeks, 4, weeks or longer.

In the tenth aspect of the invention, upon application of a photocatalyst composition, the concentration of semivolatile organic chemicals absorbed in the porous, solid material are reduced by at least 10%, and more preferably by at least, 20%, 30%, 40%, 50%, 60%, 70%, 80%, 90% or greater.

In order to accurately clarify the invention, the following terms have the following associated meanings:

"Semivolatile organic chemicals" means those organic chemical compounds containing at least one carbon to carbon bond and having a boiling point greater than 250° C. with a corresponding vapor pressure of less than 400 PA at room temperature. They do not volatilize immediately upon contamination of the building material yet they volatilize slowly thus contaminating the indoor air over the course of many years. "Photocatalyst" means those chemical substances, which in the presence of an ultraviolet light source of appropriate wavelength and intensity, will facilitate a chemical reaction between two or more chemical compounds. Whereby facilitate means that the overall reaction rate is at least twice as fast as the overall reaction rate in the absence of either the photocatalyst or the appropriate ultraviolet light source. "Porous, solid material" means those materials that have a structure such that semivolatile organic chemicals applied to the surface of that material may diffuse through the opening or pores in the structure into the interior of the material. The pores must be present in a unified quantity of the material as opposed to being the result of void spaces located between multiple unified quantities of the material. Whereby the pore sizes of the material are less than 1 micrometer. The pore size of mature concrete is between about 0.003 and 0.1 micrometer. (H. F. Taylor. Cement Chemistry, 2$^{nd}$ Ed. T. Telford, London, 1998). The pores of wood are larger, but they periodically narrow down to only about 0.2 micrometer, forming pointed-end pores. (J. Siau, *Wood: Influence of Moisture on Physical Properties*, Springer Verlag, Berlin 1995; Tsuchikawa S. and H. W. Siesler. Applied Spectroscopy, 2003, 57, 667-674; T. A. Burnes, R. A. Blanchette, and R. L. Farrell, Applied and Environ. Microbiol. 2000, 66, 5201-5205).

"Nonporous, solid material" means those materials that do not have microscopic-size pores (i.e. bigger than 1 micrometer) within the particles. For example, according to this definition sand is a nonporous solid material. The pores found in sand are the result of void space located between particles of the sand with the actual $SiO_2$ particles having essentially no pores.

"Excite" means the act of increasing the energy of a chemical by a measurable quantity at the molecular level.

"Light source" means a device, manmade or naturally occurring, that emits photons at wavelengths in the visible or ultraviolet range.

"Breakdown" means the cleavage of at least one carbon to carbon bond in an organic chemical resulting in at least two chemicals having a smaller number of carbon atoms in their molecular structure than the original.

"Photocatalyst composition" means a composition containing an effective amount of photocatalyst to reduce the amount of semivolatile organic chemicals in porous, solid material by at least 10% upon exposure to an ultraviolet light source under aerobic conditions. More preferably, the semivolatile organic chemicals are reduced by 20%, 30%, 40%, 50% or greater.

Semivolatile organic chemicals, dinitrotoluene (herein known as DNT) and n-hexadecane, were used as model systems to assess the efficiency and effectiveness of their removal from concrete and wood. The present invention, however, is not limited to these semivolatile organic chemicals. Other semivolatile organic chemicals with a vapor pressure of 400 Pa or less may be used. For example, compounds such as fuel oil/diesel/kerosene hydrocarbons (such as hexadecane), oxygenated compounds (such as diethyl phthalate), polychlorobiphenyls, halogenated compounds (such as DDT, chlordane, chlorinated dioxins and dibenzophanes), nitrocompounds (such as nitroglycerin, di- or trinitrotoluene) and other industrial compounds may be used. Semivolatile organic chemicals include products that are used in industrial, home, commercial and other applications such as petroleum fractions, insecticides, pesticides, and chemical warfare reagents.

Titanium dioxide (herein known as $TiO_2$) for concrete and wood samples and lignin for wood samples were used as model chemical and biological photocatalysts, respectively. Other photocatalysts include, but are not limited to, vanadium (V) oxide, $La_2Ti_2O_7$, and most semiconductors. Possible light sources include any type of light that falls in the range of about 150 nanometers to about 350 nanometers. Some light sources that emit light that falls within this range include, but are not limited to, ultraviolet light, fluorescent light, and natural light.

The present invention found that absorbed semivolatile organic chemicals are reduced upon as little as one day in concrete and wood, and upon further exposure, the vast majority of the remaining contaminants are reduced. Specific examples of the invention are described herein.

EXAMPLE 1

Photocatalyst-Induced Reduction of Semivolatile Organic Chemicals Absorbed in Concrete Extraction protocols were developed to accurately determine the removal of n-hexadecane and DNT from concrete samples. Using these protocols, the effectiveness of photocatalyst-induced removal of semivolatile hydrocarbons from concrete in bench-scale samples were examined. The photocatalyst, $TiO_2$ (Anatase), was obtained from Degussa, Inc. and slurried into a paste with water in a 1:1 volume-to-volume ratio. Concrete samples were generated with standard building grade cement, aggregate, sand, and water to a standard compression strength of 3000 psi. The approximate size of the concrete was 3 cm×3 cm×3 cm.

The contaminated piece of concrete was submerged into the slurry for about 5 seconds to about 10 seconds and allowed to air dry. To measure the reduction of semivolatile hydrocarbons, $^{14}C$-labeled n-hexadecane and DNT were used throughout the experiments. The reduction concentrations of the radiolabeled contaminants (DNT or n-hexadecane) were monitored for about 4 days to about 28 days upon continuous exposure to light within the about 150 nanometer to about 350 nanometer range. Prior to the extraction, samples were manually ground in a mortar until only pebbles were visually seen.

For the extraction of DNT from concrete, about 10 milliliters of 0.5 M HCl was added and the samples were shaken on a rotary shaker for about 4 days. Then, the concrete dust was centrifuged down and the first solvent was decanted and about 10 milliliters of isopropanol was added. The samples were incubated on a rotary shaker for about 2 more days. The aliquots of both fractions were analyzed taking into account the residual radioactivity of the corresponding blanks (vials with distilled water). Controls, concrete samples aged about 3 weeks, showed an extraction efficiency of about 100%.

For the extraction of n-hexadecane from the concrete sample, about 10 milliliters of n-pentane was added and the samples were shaken on a rotary shaker for about 4 days. The aliquot was analyzed taking into account the residual radioactivity of the corresponding blanks. After the extraction, scintillation counting of the radiolabeled hydrocarbons, either DNT or n-hexadecane, was performed using a Beckman 6800 counter in plastic vials using about 5 milliliters of Econo-safe scintillation cocktail. For the controls, concrete samples aged 3 weeks, the extraction efficiency was about 95%.

To assess the efficiency of contaminant reduction, same-size concrete pieces were used. The aliquot sizes of the applied contaminants were as follows: hexadecane, 5 μL of a 100 g/L solution in n-octane and DNT, 25 μL of a 170 g/L solution in ethanol. The samples were irradiated with UV light, with and without the photocatalyst ($TiO_2$), and the contaminant's concentration was determined by extraction followed by scintillation counting. As shown in Table IA, irradiation of concrete with fluorescent or UV light resulted in about a 70% removal of DNT after about 3-4 weeks. While samples treated without a catalyst retained about 95% or greater of the chemical contaminant. Similarly, irradiation of concrete with a fluorescent or UV light resulted in about 90% reduction of n-hexadecane between about 3-4 weeks (Table IB).

TABLE I

Photocatalyst Reduction of Semivolatile Organic Chemicals in Concrete

| Photocatalyst | Light source | % Removed from Concrete | | | |
|---|---|---|---|---|---|
| | | 1 day | 7 days | 14 day | 28 day |
| A. Dinitrotoluene (DNT) | | | | | |
| None | none | 0 | 0 | 0 | 0 |
| None | UV light | 0 | 10 | 25 | 25 |
| $TiO_2$ | Fluorescent | 7 | 15 | 30 | 72 |
| $TiO_2$ | UV light | 6 | 22 | 28 | 68 |
| B. n-Hexadecane | | | | | |
| None | none | 0 | 0 | 0 | 0 |
| None | UV light | 0 | 10 | 35 | 55 |
| $TiO_2$ | Fluorescent | 14 | 43 | 76 | 88 |
| $TiO_2$ | UV light | 18 | 58 | 81 | 91 |

Without the presence of the photocatalyst, a slow reduction of the amounts of contaminants occurred as well (apparently, concrete contains some low-efficiency photocatalysts-semiconductors). However, in addition to accelerating the removal, the presence of the photocatalyst ($TiO_2$) was essential for the conversion of the pollutant selectively to carbon dioxide and water. The conversion to carbon dioxide and water was demonstrated by placing the samples in a sealed apparatus and subsequently trapping the volatilized organic chemicals.

The experiment was based on the removal of $^{14}C$-labeled hexadecane from concrete using $TiO_2$ as the photocatalyst in the presence of $CO_2$-free air pushed through the test system. Volatilized organic chemicals in the gaseous phase were selectively adsorbed on a hydrophobic DAX resin that absorbs organic chemicals but does not adsorb $^{14}CO_2$. Afterwards, the air was passed through isopropylamine, which absorbs $^{14}CO_2$. About one sixth of the $^{14}C$ from the gaseous phase was recovered on the DAX resin and the remainder was recovered in the isopropylamine trap as $^{14}CO_2$. Subsequent mass-spectrometry analysis revealed that the only organic chemical present on the DAX resin was hexadecane itself, and no oxidation by-products. A similar experiment was conducted without a photocatalyst, showing numerous organic by-products that were recovered on the DAX resin and that the amount of absorbed $^{14}CO_2$ was substantially reduced.

EXAMPLE 2

Photocatalyst-Induced Reduction of Semivolatile Organic Chemicals Absorbed in Wood Extraction protocols were developed to accurately determine the removal of n-hexadecane and DNT from wood samples. Using these protocols, the effectiveness of the photocatalyst-enhanced removal of semivolatile hydrocarbons from wood samples was examined. The reduction in concentrations of radiolabeled hydrocarbons (DNT or n-hexadecane) in wood samples was monitored for about 4 days to about 28 days.

For the chemical catalyst studies, $TiO_2$ (Anatase) was obtained from Degussa, Inc. and slurried into a paste with water in a 1:1 volume-to-volume ratio. The contaminated piece of wood was submerged into the slurry for about 5 seconds to about 10 seconds and allowed to air dry. For the biological studies, roughening the surface of the wood such as with sandpaper, in order to expose some of the wood fibers, resulted in a quicker initial lignin exposure. In another embodiment, a material with lignin exposed (i.e. wood chips or saw dust) may be placed on the surface of any type of porous, solid surface. The lignin was exposed to a light source (150 nm-350 nm range) in order to serve as the photocatalyst.

Wood samples of about 3 cm wide by about 3 cm long by about 1 cm thick were generated from Southern yellow pine and used in all experiments. $^{14}C$-labeled n-hexadecane and DNT were used throughout the experiments. After treatment and exposure, the wood was ground in a Wiley mill manually or using a coffee grinder until the largest piece was about 2 millimeters or less. For the extraction of DNT from wood, about 10 milliliters of dichloromethane was used and the samples were shaken on a rotary shaker for about 4 days. After about 4 days had elapsed, the first solvent was decanted. Next, about 10 milliliters of dimethylsulfoxide was added and the samples were incubated on a rotary shaker for about 2 more days. The aliquots of both fractions were analyzed to determine the remaining radioactivity. For controls, samples aged for about 3 weeks, the extraction efficiency was about 100%.

For the extraction of n-hexadecane from wood, about 10 milliliters of acetone was used; the samples were shaken on a rotary shaker for about 4 days. After about 4 days, the first solvent was decanted and about 10 milliliters of n-pentane was added. The samples were incubated on a rotary shaker for about 2 additional days. For controls, samples aged 3 weeks, the extraction efficiency was about 95%.

Scintillation counting for the radiolabeled hydrocarbons (DNT or n-hexadecane) was performed using a Beckman 6800 counter in plastic vials using about 5ml of Econo-safe scintillation cocktail.

As shown in Table IIA, irradiation of wood treated with $TiO_2$ and a light source emitting light within the specified range (about 150 nm to about 350 nm), resulted in about 50-55% removal of DNT after about 3-4 weeks. Samples treated by exposing endogenous lignin as the photocatalyst were reduced by about 60%. Similarly, using either $TiO_2$ or endogenous lignin followed by irradiation of wood with a light source emitting light within the specified range (about 150 nm to about 350 nm), resulted in about 90% or greater reduction of n-hexadecane between about 3-4 weeks (Table IIB).

TABLE II

Photocatalyst Reduction of Semivolatile Organic Chemicals in Wood

| Photocatalyst | Light source | % Removed from Wood | | | |
|---|---|---|---|---|---|
| | | 1 day | 7 days | 14 day | 28 day |
| A. Dinitrotoluene | | | | | |
| None | none | 0 | 0 | 0 | 0 |
| $TiO_2$ | Fluorescent | 7 | 15 | 40 | 50 |
| Lignin | Fluorescent | 7 | 18 | 47 | 61 |
| $TiO_2$ | UV light | 6 | 22 | 42 | 55 |
| B. n-Hexadecane | | | | | |
| None | none | 0 | 0 | 0 | 0 |
| $TiO_2$ | Fluorescent | 2 | 85 | 88 | 92 |
| Lignin | Fluorescent | 10 | 58 | 85 | 88 |
| $TiO_2$ | UV light | 3 | 80 | 92 | 97 |

The presence of a light source emitting light within the specified range (about 150 nm to about 350 nm), is essential. When the experiments were conducted in a glass flask that did not let light of the specified range through, virtually 100% DNT remained in the wood and virtually no $^{14}CO_2$ was recovered.

The variables that may decrease the rate of reduction of contaminants' in solid porous materials by irradiation in the presence of photocatalysts are: (i) higher contaminant concentration in the building material, (ii) greater time elapsed between the contamination and the treatment (so-called "sample aging" leading to a stronger adsorption of the contaminant within the pores), (iii) saturation of the building material with water, and (iv) any combination of these factors. For example, saturating the pores of wood with water after the contamination and/or the "aging" of DNT contamination by about 6 weeks resulted in a decrease of removal efficiency after the treatment with the light source for about 14-28 days. The decrease was in the order of about 30% less efficiency. For hexadecane, the removal efficiency dropped about 17% under similar conditions.

EXAMPLE 3

Photocatalyst-Induced Reduction of Different Chain Length Semivolatile Organic Chemicals Absorbed in Wood Experiments were conducted to create the "worst-case scenario" characteristic for a building contamination, as a result of flooding or fuel oil tank rupture. Wood samples were saturated with a large amount of pollutants (fuel oil, 100 μL, i.e., 20 times the amounts discussed earlier). Samples of hydrocarbons having varied chain lengths were tested. Afterwards, the samples were inundated with water and "aged" for about 6 weeks. The "aging" process hinders the diffusion of chemicals toward the surface. After the aging was complete, the wood samples were treated with $TiO_2$ and UV light as described in Example 2 for about 6 weeks (Table III). The same extraction procedure that was used for hexadecane was also used for quantifying the results found in Table III. The analytical method for monitoring the fuel oil concentration was done using gas chromatography, which allows for the separation of straight-chain saturated aliphatic hydrocarbons, used to identify the major components of fuel oil.

TABLE III

Percentage of Removal from Contaminated Wood for Individual Non-branched Hydrocarbons of Fuel Oil (determined by gas chromatography) After 5, 28, and 42 Days of Incubation.

| | Hydrocarbon Chain Length | | | | | | | | |
|---|---|---|---|---|---|---|---|---|---|
| | $C_{14}$ | $C_{15}$ | $C_{16}$ | $C_{17}$ | $C_{18}$ | $C_{19}$ | $C_{20}$ | $C_{21}$ | $C_{22}$ |
| 5 days | | | | | | | | | |
| UV, $TiO_2$ | 76 ± 2 | 59 ± 9 | 48 ± 28 | 26 ± 11 | 21 ± 17 | 0 | 0 | 0 | 0 |
| No treatment | 59 ± 6 | 36 ± 19 | 0 | 0 | 0 | 0 | 0 | 0 | 0 |
| 14 days | | | | | | | | | |
| UV, $TiO_2$ | 92 ± 1 | 81 ± 4 | 61 ± 16 | 43 ± 14 | 36 ± 18 | 21 ± 4 | 16 ± 7 | 0 | 0 |
| No treatment | 80 ± 3 | 62 ± 9 | 7 ± 5 | 0 | 0 | 0 | 0 | 0 | 0 |
| 42 Days | | | | | | | | | |
| UV, $TiO_2$ | 100 | 100 | 87 ± 5 | 67 ± 1 | 48 ± 9 | 33 ± 6 | 28 ± 1 | 21 ± 3 | 11 ± 6 |
| No treatment | 100 | 92 ± 2 | 72 ± 10 | 44 ± 6 | 13 ± 7 | 0 | 0 | 0 | 0 |

The $C_{14}$ through $C_{18}$ fractions were substantially reduced during the first 5 days, relative to untreated controls. The loss observed in the controls was due to the natural evaporation of semivolatile organic contaminants in an aerobic environment over the course of time. In contrast, it was only after 42 days of treatment that the longer chain fractions ($C_{19}$ through $C_{22}$) were reduced, while no loss was observed for untreated controls. The data presented above shows the significance of the light source/$TiO_2$ treatment for the accelerated removal of different chain length semivolatile contaminants. Most preferably, the suggested light source/photocatalytic treatment successfully removes the most dangerous fraction of semivolatile hydrocarbons that otherwise would remain within the building material for a long time and would slowly pollute the surrounding air.

The description of the specific embodiments of the invention is presented for the purposed of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims.

The invention claimed is:

1. A method of accelerating reduction of a concentration of a semivolatile organic chemical from interior pores of a porous, solid building material, the method comprising:
    exposing a photocatalyst on a surface of the porous, solid building material to a light source under aerobic conditions; and
    degrading the semivolatile organic chemical with the photocatalyst as the semivolatile organic chemical diffuses from the interior pores of the porous, solid building material towards the surface of the porous, solid building material until an amount of removal of the semivolatile organic chemical is achieved, wherein the semivolatile organic chemical comprises compounds having vapor pressures less than 200 Pa at room temperature.

2. The method of claim 1, wherein the semivolatile organic chemical comprises compounds having a vapor pressure less than 100 Pa at room temperature.

3. The method of claim 2, wherein the semivolatile organic chemical is selected from a group consisting of fuel oil, diesel, kerosene hydrocarbons, oxygenated compounds, polychlorobiphenyls, halogenated compounds, nitrocompounds, and any combinations thereof.

4. The method of claim 1, wherein the porous, solid building material is selected from a group consisting of concrete, wood, lumber, gypsum, brick, masonry, asphalt, cement, cinder, tile, drywall, and any combinations thereof.

5. The method of claim 1, wherein the photocatalyst is selected from a group consisting of biological photocatalysts, chemical photocatalysts, and any combinations thereof.

6. The method of claim 5, wherein the chemical photocatalyst is selected from a group consisting of titanium dioxide, vanadium oxide, $La_2Ti_2O_7$, Tinolux BBS, and any combinations thereof.

7. The method of claim 5, wherein the biological photocatalyst is lignin that is exposed by abrading the surface of the porous, solid building material wherein the porous, solid building material is selected from a group consisting of wood, lumber, and any combinations thereof.

8. The method of claim 7, wherein an additional source of lignin is added onto the surface of the porous, solid material.

9. The method of claim 1, wherein the light source comprises any type of light that emits light in the range of about 150 nanometers to about 350 nanometers.

10. The method of claim 1, wherein the light source is chosen from a group consisting of fluorescent light, ultraviolet light, natural light and any combinations thereof.

11. The method of claim 2, wherein the semivolatile organic chemical comprises compounds having a vapor pressure less than 50 Pa at room temperature.

12. The method of claim 1, wherein the semivolatile organic chemical comprises compounds having a boiling temperature greater than 250° C.

13. The method of claim 5, wherein the biological photocatalyst is lignin.

14. A method of reducing an amount of a semivolatile organic chemical found in interior pores of a porous, solid building material, the method comprising:
    preparing a surface of the porous, solid building material to have an exposed photocatalyst on the surface;
    activating the photocatalyst under aerobic conditions; and
    degrading the semivolatile organic chemical with the photocatalyst as the semivolatile organic chemical diffuses from the interior pores of the porous, solid building material towards the surface of the porous, solid building material, wherein the semivolatile organic chemical comprises compounds having vapor pressures less than 200 Pa at room temperature.

15. The method of claim 14, wherein the semivolatile organic chemical comprises compounds having a vapor pressure less than 100 Pa at room temperature.

16. The method of claim 15, wherein the semivolatile organic chemical is selected from a group consisting of fuel oil, diesel, kerosene hydrocarbons, oxygenated compounds, polychlorobiphenyls, halogenated compounds, nitrocompounds, and any combinations thereof.

17. The method of claim 14, wherein the porous, solid building material is selected from a group consisting of concrete, wood, lumber, gypsum, brick, masonry, asphalt, cement, cinder, tile, drywall, and any combinations thereof.

18. The method of claim 14, wherein the photocatalyst is selected from a group consisting of biological photocatalysts, chemical photocatalysts, and any combinations thereof.

19. The method of claim 18, wherein the chemical photocatalyst is selected from a group consisting of titanium dioxide, vanadium oxide, $La_2Ti_2O_7$, Tinolux BBS, and any combinations thereof.

20. The method of claim 18, wherein the biological photocatalyst is lignin that is exposed by abrading the surface of the porous, solid building material wherein the porous, solid building material is selected from a group consisting of wood, lumber, and any combinations thereof.

21. The method of claim 14, wherein the photocatalyst is activated by light having wavelengths between about 150 nanometers to about 350 nanometers.

22. The method of claim 21, wherein the light is chosen from a group consisting essentially of fluorescent light, ultraviolet light, natural light and any combinations thereof.

23. A method for accelerating reduction of a semivolatile organic chemical from interior pores of a porous, solid building material, the method comprising:
    applying a photocatalyst onto a surface of the porous, solid building material;
    activating the photocatalyst with a light source; and
    degrading the semivolatile organic chemical with the photocatalyst as the semivolatile organic chemical diffuses from the interior pores of the porous, solid building material towards the surface of the porous, solid building material, wherein the semivolatile organic chemical comprises compounds having vapor pressures less than 200 Pa at room temperature.

24. The method of claim 23, wherein the semivolatile organic chemical comprises compounds having a vapor pressure less than 100 Pa at room temperature.

25. The method of claim 11, wherein the semivolatile organic chemical comprises compounds having a vapor pressure less than 10 Pa at room temperature.

26. The method of claim 15, wherein the semivolatile organic chemical comprises compounds having a vapor pressure less than 50 Pa at room temperature.

27. The method of claim 26, wherein the semivolatile organic chemical comprises compounds having a vapor pressure less than 10 Pa at room temperature.

28. The method of claim 24, wherein the semivolatile organic chemical comprises compounds having a vapor pressure less than 50 Pa at room temperature.

29. The method of claim 28, wherein the semivolatile organic chemical comprises compounds having a vapor pressure less than 10 Pa at room temperature.

* * * * *

UNITED STATES PATENT AND TRADEMARK OFFICE
CERTIFICATE OF CORRECTION

Page 1 of 1

PATENT NO. : 7,781,638 B2
APPLICATION NO. : 11/209144
DATED : August 24, 2010
INVENTOR(S) : Evguenii I. Kozliak and Wayne Seames It is certified that error appears in the above-identified patent and that said Letters Patent is hereby corrected as shown below:

Col. 10, Line 49
Delete "essentially"

Signed and Sealed this
Fifth Day of July, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,781,638 B2 | Page 1 of 1 |
| APPLICATION NO. | : 11/209144 | |
| DATED | : August 24, 2010 | |
| INVENTOR(S) | : Evguenii I. Kozliak and Wayne Seames | |

It is certified that error appears in the above-identified patent and that said Letters Patent is hereby corrected as shown below:

Col. 1, line 4, please add the following Statement of Government Interest:

STATEMENT OF GOVERNMENT INTEREST
This invention was made with government support under Contract No. 03-JV-11111120-137 awarded by the United States Department of Agriculture. The government has certain rights in the invention.

Signed and Sealed this
First Day of January, 2013

David J. Kappos
*Director of the United States Patent and Trademark Office*